(12) United States Patent
Bruns et al.

(10) Patent No.: US 9,102,594 B2
(45) Date of Patent: Aug. 11, 2015

(54) METHOD FOR PRODUCING ISOCYANATES IN THE GAS PHASE

(75) Inventors: Rainer Bruns, Leverkusen (DE); Wolfgang Lorenz, Dormagen (DE); Andreas Karl Rausch, Kaarst (DE); Stefan Wershofen, Mönchengladbach (DE); Tim Loddenkemper, Dormagen (DE)

(73) Assignee: Bayer Intellectual Property GmbH (DE)

( * ) Notice: Subject to any disclaimer, the term of this patent is extended or adjusted under 35 U.S.C. 154(b) by 0 days.

(21) Appl. No.: 13/696,195

(22) PCT Filed: Apr. 29, 2011

(86) PCT No.: PCT/EP2011/056848
§ 371 (c)(1),
(2), (4) Date: Jan. 18, 2013

(87) PCT Pub. No.: WO2011/138245
PCT Pub. Date: Nov. 10, 2011

(65) Prior Publication Data
US 2013/0131377 A1   May 23, 2013

(30) Foreign Application Priority Data

May 5, 2010   (DE) .......................... 10 2010 019 342

(51) Int. Cl.
*C07C 263/10* (2006.01)
(52) U.S. Cl.
CPC ..................... *C07C 263/10* (2013.01)
(58) Field of Classification Search
CPC combination set(s) only.
See application file for complete search history.

(56) References Cited

U.S. PATENT DOCUMENTS

| | | | |
|---|---|---|---|
| 4,847,408 A | 7/1989 | Frosch et al. | |
| 5,391,683 A | 2/1995 | Joulak et al. | |
| 5,633,396 A | 5/1997 | Bischof et al. | |
| 5,872,292 A | 2/1999 | Adkins et al. | |
| 2004/0068137 A1 | 4/2004 | Herold et al. | |
| 2005/0022940 A1 | 2/2005 | Kupper et al. | |
| 2008/0146834 A1 | 6/2008 | Pohl et al. | |
| 2008/0167490 A1 | 7/2008 | Pohl et al. | |
| 2009/0149671 A1* | 6/2009 | Stutz et al. | 560/347 |
| 2009/0221846 A1 | 9/2009 | Wolfert et al. | |
| 2010/0210870 A1 | 8/2010 | Olbert et al. | |
| 2010/0312009 A1 | 12/2010 | Sanders et al. | |
| 2012/0046497 A1 | 2/2012 | Stroefer et al. | |

FOREIGN PATENT DOCUMENTS

| | | |
|---|---|---|
| DE | 102005036870 A1 | 2/2007 |
| EP | 289840 B1 | 10/1990 |
| EP | 0593334 B1 | 5/1997 |
| EP | 0749958 B1 | 10/1999 |
| EP | 0954549 B1 | 9/2002 |
| EP | 1403248 B1 | 5/2006 |
| EP | 1935876 A1 | 6/2008 |
| EP | 2060560 A1 | 5/2009 |
| EP | 1935875 B1 | 7/2011 |
| JP | 2009-149614 A | 7/2009 |
| WO | WO-2005016512 A1 | 2/2005 |
| WO | WO-2005010066 A3 | 3/2005 |
| WO | WO-2009027232 A1 | 3/2009 |
| WO | WO-2009077795 A1 | 6/2009 |
| WO | WO-2010121997 A1 | 10/2010 |

OTHER PUBLICATIONS

"Nitrogen" in Kirk-Othmer Encyclopedia of Chemical Technology, Hardenburger et al., Published Online: May 13, 2005, Copyright © 2001 by John Wiley & Sons, Inc., pp. 1-23.*
International Search Report for PCT/EP2011/056848 mailed Aug. 4, 2011.
Translation of the International Preliminary Report on Patentability for PCT/EP2011/056848 dated Nov. 6, 2012.

* cited by examiner

*Primary Examiner* — Karl J Puttlitz
(74) *Attorney, Agent, or Firm* — Drinker Biddle & Reath LLP

(57) ABSTRACT

The invention relates to a process for the preparation of isocyanates by reaction of the corresponding amines with phosgene in the gas phase, wherein a diluent containing between 90.0000% by weight and 99.9999% by weight of substances which are inert in the phosgenation process and between 0.0001% by weight and 10.0000% by weight of oxygen is present during the conversion of the amine into the gas phase and the molar ratio of amine to oxygen ($O_2$) is $\geq 1,000:1$.

11 Claims, No Drawings

METHOD FOR PRODUCING ISOCYANATES IN THE GAS PHASE

CROSS-REFERENCE TO RELATED APPLICATIONS

This application is a national stage application (under 35 U.S.C. §371) of PCT/EP2011/056848, filed Apr. 29, 2011, which claims benefit of German Application No. 10 2010 019 342.9, filed May 5, 2010, both of which are incorporated herein by reference in their entirety.

The invention relates to a process for the preparation of isocyanates by reaction of the corresponding amines with phosgene in the gas phase, wherein a diluent containing between 90.0000% by weight and 99.9999% by weight of substances which are inert in the phosgenation process and between 0.0001% by weight and 10.0000% by weight of oxygen ($O_2$) is present during the conversion of the amine into the gas phase and the molar ratio of amine to oxygen ($O_2$) is ≥1,000:1.

Isocyanates, and in particular diisocyanates, are prepared in large amounts and serve chiefly as starting substances for the preparation of polyurethanes. They are usually prepared by reaction of the corresponding amines with phosgene. The reaction of the amines with phosgene can be carried out in the liquid phase or by phosgenation in the gas phase.

The present invention relates exclusively to phosgenation in the gas phase.

This process procedure is distinguished in that the reaction conditions are chosen such that at least the reaction components amine, isocyanate and phosgene, but preferably all the educts, products and reaction intermediate products, are gaseous under the reaction conditions chosen. Advantages of gas phase phosgenation are, inter alia, a reduced phosgene hold-up, the avoidance of intermediate products which are difficult to phosgenate and increased reaction yields.

Various processes for the preparation of diisocyanates by reaction of diamines with phosgene in the gas phase are known from the prior art.

EP 0 289 840 B1 discloses for the first time a process for the preparation of aliphatic diisocyanates by phosgenation of the corresponding diamines in the gas phase, in which the vaporous diamines, optionally diluted with an inert gas or with the vapours of an inert solvent, and phosgene are heated separately from one another to temperatures of from 200° C. to 600° C. and are reacted with one another continuously in a reaction space heated to 200° C. to 600° C. The preferred inert gas is nitrogen. Suitable inert solvents, the vapours of which can likewise be used for dilution of the diamine, are monochlorobenzene, ortho-dichlorobenzene, xylene, chloronaphthalene, decahydronaphthalene or mixtures thereof. According to this specification, the amount of inert gas or solvent vapour optionally co-used as a diluent is not critical. If dilution of the diamine takes place, this can be carried out, for example, while maintaining a volume ratio of diamine vapour to inert gas or solvent vapour of from 1:0.5 to 1:2. Beyond the requirement that the diluent is to be inert, no further information is given on the purity thereof.

EP 0 593 334 B1 describes for the first time a process for the preparation of aromatic diisocyanates in the gas phase. In this, the reactants brought into contact during the reaction, i.e. at least one diamine and phosgene, can be employed by themselves or in the presence of a diluting gas stream. A diluting gas stream ("gas dilution vector") in this context is understood as meaning any gas which has a diluting effect and is inert towards the reaction participants and reaction products. Apart from the inert gases, such as, in particular, nitrogen, the vapour of a solvent, in particular benzene, xylene, monochlorobenzene or ortho-dichlorobenzene, can also be used. Beyond the requirement that the diluting gas stream is to be inert, no further information is given on the purity thereof.

The use of diluents (inert gases or the vapours of inert solvents) for dilution of the educts amine and/or phosgene is thus prior art. In particular, dilution of the amine is general practice. The reason for this is that suitable inert substances, often nitrogen, act as entraining agents and facilitate vaporization of the amine, as a result of which decomposition reactions (for example with splitting off of ammonia) are reduced. Thus, for example, the addition of even small amounts of nitrogen to toluoylenediamine (as a rule a mixture of various isomers, summarized by the abbreviation TDA in the following) has the effect of significantly reducing the vaporization temperature. For example, the addition of 4% by weight of nitrogen leads to a reduction in the vaporization temperature of TDA by approx. 8K. Small amounts of a diluent are thus already sufficient to lower the vaporization temperature. The substance added to lower the boiling point should be inert towards the amine and the later reaction products and/or intermediate products, because a reaction of the amine and/or the reaction products and/or the reaction intermediate products with the auxiliary substance on the one hand would narrow the yield with respect to amine and on the other hand could lead to formation of deposits and/or make purification of the isocyanate by distillation difficult. It is also known that substances having an oxidizing action can change the properties of an isocyanate such that discolorations occur in the isocyanate itself or in the resulting polyurethane foam (see e.g. WO 2005/010066, page 1, line 24 to 26).

According to the prior art, nitrogen is one of the diluents preferably employed for lowering the temperature required for vaporization of the amine Technical grade nitrogen is obtainable in various purities and accessible by various preparation processes. In the majority of processes for obtaining nitrogen, air is used as the starting substance. Frequent processes for dissociation of air are cryodistillation, membrane processes and alternating pressure adsorption. Cryodistillation is the most effective technology for production of large amounts of nitrogen. Alternating pressure adsorption and membrane processes are the more economical processes for the production of less pure nitrogen (up to 99.8% purity with a minimal residual oxygen of 0.2%) with average volume flows (25-500 $Nm^3/h$). In order to achieve higher purities, an additional deoxo system must be employed for removal of oxygen by reaction with hydrogen with subsequent drying of the gas. Such deoxo systems, however, can lead to hydrogen remaining in the nitrogen, and they are associated with significant costs for the hydrogen supply and the deoxo installation itself (Kirk-Othmer Encyclopedia of Chemical Technology, 2001 by John Wiley & Sons, Inc., "Nitrogen" chapter). The required amount of nitrogen and above all the required purity of the nitrogen thus has a substantial influence on the choice of the process for the preparation of the nitrogen (see loc. cit., Figure 1) and therefore on the costs to be taken into account for the nitrogen supply if nitrogen is to be employed as the diluent in a process for the preparation of isocyanates in the gas phase. As soon as purities of less than 99.9 vol. % are acceptable, several processes can be chosen for producing the nitrogen. If a purity of less than 93 vol. % is even acceptable, there is the advantage that a cryodistillation in a single-column apparatus which produces nitrogen with an oxygen content of 7 vol. % can be employed (Linde AG: Cryogenic dissociation of air, origin and technical development).

Noble gases can likewise be employed according to the prior art as a diluent, argon, which is the least expensive noble gas, being mentioned in particular. Argon, like nitrogen, is obtained by dissociation of air, in particular by cryodistillation. Since argon boils at only 3K lower than oxygen, the preparation of low-oxygen argon in turn only succeeds by the use of subsequent steps for removal of oxygen, such as selective adsorption, reaction with hot metal or by catalysed reaction with hydrogen to give water and subsequent drying. The argon purity can indeed by increased from 98% after the cryodistillation to up to 99.999% by these steps, but high costs are thus necessary for the additional installations and operation and maintenance thereof (Kirk-Othmer Encyclopedia of Chemical Technology, 2001 by John Wiley & Sons, Inc., "Noble gases" chapter).

In conventional technical grade purities, "inert" organic solvents likewise contain certain amounts of dissolved oxygen. Without particular measures, oxygen is therefore also present in the vapours of organic solvents which can be employed according to the prior art as diluents which facilitate the vaporization of the amine.

It is known to the person skilled in the art that oxygen is not inert towards amines, but a rapid and irreversible reaction can occur which leads to discoloration of he amine EP 0 954 549 B1 thus describes, in paragraph [0002], that compounds containing amino groups generally tend to discolour in contact with oxygen. It is thus stated, for example, for ortho-toluenediamine, such as 2,3-diaminotoluene or 3,4-diaminotoluene, that this already darkens directly after the action of air, while other amines, e.g. aniline, are indeed more stable, but likewise become dark in the course of time. Aliphatic compounds with amino groups also discolour in the course of time at room temperature; in general, however, according to EP 0 954 549 B1 these discolour at a very much slower speed than aromatic compounds containing amino groups.

The person skilled in the art thus deduces from the prior art the general teaching that in the event of the use of a diluent to facilitate the vaporization of the amine, this diluent must have a very high purity, in particular a very low content of oxygen, since side reactions of the amine with the oxygen otherwise occur.

These limitations are a disadvantage, since as a result on the one hand the costs for obtaining and monitoring the quality of the diluent, e.g. nitrogen or argon, increase and on the other hand the flexibility of the process for the preparation of isocyanates in the gas phase suffers, since the diluent to be employed must be available in a high purity, which, depending on the location, can be realized only with a high logistics outlay.

The object of the present invention was therefore to provide a process for the preparation of isocyanates by reaction of the corresponding amines with phosgene in the gas phase, in which a substance which is inert in the phosgenation process can be employed in order to facilitate the conversion of the amine into the gas phase, without the purity requirements on the substance which is inert in the phosgenation process adversely influencing the profitability of the process.

It has been found, surprisingly, that the object can be achieved by a process for the preparation of isocyanates by reaction of the corresponding amines with phosgene in the gas phase, wherein (i) the amine is converted into the gas phase in a vaporization space in the presence of from >0.10% by weight to 25% by weight, preferably from >0.10% by weight to 10% by weight, particularly preferably from >0.20% by weight to 5.0% by weight of a diluent containing at least one substance which is inert in the phosgenation process, based on the total weight of diluent and amine;

(ii) the gaseous stream obtained from (i) containing amine and diluent is reacted with a gaseous phosgene stream in a reaction space to give the corresponding isocyanate; wherein the diluent employed in step (i) contains between 90.0000% by weight and 99.9999% by weight, preferably between 99.0000% by weight and 99.9950% by weight, particularly preferably between 99.5000% by weight and 99.9900% by weight of substances which are inert in the phosgenation process and between 0.0001% by weight and 10.0000% by weight, preferably between 0.0050% by weight and 1.0000% by weight, particularly preferably between 0.0100% by weight and 0.5000% by weight of oxygen, in each case based on the weight of the diluent; and the molar ratio of amine to oxygen ($O_2$) in step (i) in the vaporization space is ≥1,000:1 and is preferably in the range between 1,000:1 and 1,000,000:1, particularly preferably between 10,000:1 and 50,000:1.

"Reaction in the gas phase" is to be understood as meaning that the amines react in the gaseous state to give the isocyanates and in the course of the reaction all the components present (educts, products, intermediate products, any by-products, any inert substances) remain in the gas phase during passage through the reaction space to the extent of at least 95.0% by weight, preferably to the extent of at least 98.0% by weight, particularly preferably to the extent of at least 99.0% by weight and very particularly preferably to the extent of at least 99.9% by weight, in each case based on the total weight of all the components present.

"Vaporization space" in this context is understood as meaning the space in which the primary amine is converted into the gas phase. The vaporization space is in a technical device for conversion of liquids into the gas phase, the vaporizer. In the simplest case the vaporization space is identical to the internal volume of the vaporizer.

A "substance which is inert in the phosgenation process" (called "inert substance" in the following for simplification) in the context of the invention is a substance which is present in gaseous form in the reaction space at the reaction temperature and as such (i.e. at 100% purity—which cannot be achieved in practice) preferably does not react at all or reacts only insignificantly (i.e. without measureable impairment of the process) with the compounds occurring in the course of the reaction (amine, phosgene, intermediate products, by-products, products). The inert substance, together with the impurities it contains (as a rule exclusively or at least predominantly oxygen), forms the diluent. Mixtures of several substances which are inert in the phosgenation process can also be employed.

"Reaction space" in this context is understood as meaning the space in which the gas phase reaction of primary amine (or intermediate products) with phosgene to give the desired isocyanate takes place. This space starts where the educts are mixed for the first time and ends where the prerequisites for a gas phase reaction of primary amine (or intermediate products) with phosgene to give the desired isocyanate no longer exist (for example due to discontinuation of the reaction as a result of a lowering of the temperature or "quenching" (see below) etc.).

It is particularly surprising that the object is achieved according to the invention, because it is known that oxygen reacts with amines and therefore in no way is an inert compound or behaves inertly. On the basis of this finding, the prior art of gas phase phosgenation can be improved, since a substance of a purity lower than that conventional hitherto (i.e. with higher oxygen contents) can now be employed as the diluent during conversion of the amine into the gas phase, as a result of which the profitability of the process is improved. It is furthermore surprising that the object is achieved according to the invention, because it is known that oxygen likewise reacts with the reaction product isocyanate and is therefore not inert towards the reaction product. The diluent according to the invention is therefore a mixture of the actual inert substance and oxygen in small amounts.

It has been found, in fact, that oxygen in very small amounts, namely in amounts of less than 1,000th of the substance amount of the amine in the vaporization space, indeed react very rapidly with the amine, in agreement with the prior art, but this reaction only insignificantly influences the process for the preparation of isocyanates in the gas phase.

If the stream of gaseous amine contains oxygen in a substance amount [mol] which is less than 1,000th of the substance amount of the amine vaporized [mol], the reaction of the oxygen with the amine leads to the formation of monomeric and binary oxidation products, the boiling points of which are not substantially higher (i.e. only by a few K, in general not more than 20K, preferably not more than 10K, particularly preferably not more than 5K) than that of the original amine. The monomeric and binary oxidation products thus remain in the gas phase and enter into the reaction space for the gas phase phosgenation together with the amine stream. The monomeric and binary oxidation products react there with phosgene to give partially chlorine-containing secondary products, which have higher boiling points than the corresponding isocyanate, so that these secondary products of the monomeric and binary oxidation products remain in the so-called "high-boiling residue" of the isocyanate process. The presence of small amounts of oxygen thus leads to a slight reduction in the yield with respect to the amine, to a slightly increased formation of isocyanate residue, but not to an impairment of the vaporization of the amine or of the feeding of the gaseous amine into the reaction space. These slight losses in yield are more than compensated in the economic respect by the more favourable supply and, if appropriate in the case of recycling of the inert substance, by the lower consumption.

If the stream of vaporized amine contains oxygen in a substance amount [mol] which is greater than or equal to 1,000th of the substance amount of the amine vaporized [mol], the reaction of the oxygen with the amine also leads to high-boiling oligomeric oxidation products in addition to the monomeric and binary oxidation products. The content of oligomeric oxidation products up to tar-like products increases the higher the oxygen content in the gaseous amine rises. The oligomeric oxidation products have a boiling point which is significantly above the boiling point of the original diamine Condensation and blocking of the lines which contain gaseous amine can therefore occur. Blockages of constrictions in cross-section which cause a pressure loss have massive effects on the service life of the gas phase reactor and on the availability of the process for the preparation of isocyanates in the gas phase, and are to be rated extremely critically. Furthermore, as oxidation of the amine increases, water may also be formed as a product of the oxidation. The presence of water in the phosgenation is likewise undesirable, since decomposition of the phosgene with formation of hydrogen chloride occurs as a result, and the stoichiometry required within the reaction space is therefore adversely influenced. Phosgene losses are moreover the consequence. Water is furthermore undesirable in phosgenation reactions, since it results in the risk of corrosion if particularly high quality (and therefore particularly expensive) materials are not employed.

In a preferred embodiment of the present invention, the amine is converted into the gas phase for the purpose of the gas phase phosgenation in at least one vaporization space in the presence of a diluent containing an inert substance, and is thereby heated to temperatures of from 200° C. to 600° C., preferably 200° C. to 500° C., particularly preferably 250° C. to 450° C., and fed to the reaction space. According to the invention, a diluent which contains between 90.0000% by weight and 99.9999% by weight, preferably between 99.0000% by weight and 99.9950% by weight, particularly preferably between 99.5000% by weight and 99.9900% by weight of substances which are inert in the phosgenation process and between 0.0001% by weight and 10.0000% by weight, preferably between 0.0050% by weight and 1.000% by weight, particularly preferably between 0.0100% by weight and 0.5000% by weight of oxygen, in each case based on the weight of the diluent, is used here. If a mixture of several inert substances is employed (e.g. nitrogen and a noble gas), the abovementioned contents by weight "of inert substance" relate to the sum of all the inert substances. The diluent is employed in contents of from 0.10% by weight to 25% by weight, preferably from 0.10% by weight to 10% by weight, particularly preferably from 0.20% by weight to 5.0% by weight, based on the total weight of amine and diluent, a molar ratio of amine to oxygen ($O_2$) of ≥1,000:1, preferably in the range between 1,000:1 and 1,000,000:1, particularly preferably between 10,000:1 and 50,000:1 being maintained. In this context, the lower limits for the molar ratio of amine to oxygen in each case reflect technical effects (too low an amine:oxygen ratio leads to the adverse effects already mentioned above), while the upper limits for the molar ratio of amine to oxygen are in each case blamed on economic effects (too high an amine:oxygen ratio increases the price for the diluent disproportionately, if a very high amine:oxygen ratio is not to be achieved by greatly reducing the amount of diluent, which, however, is not possible to an unlimited extent because below a certain limit concentration, which is in general about 0.10% by weight of the diluent, based on the total weight of diluent and amine to be vaporized, a facilitated vaporization can no longer be achieved.

Possible inert substances in this context are, for example, on the one hand those substances which are already gaseous at room temperature, that is to say, for example, nitrogen, noble gases such as helium or argon, and other gases such as carbon dioxide. On the other hand—less preferably—possible inert substances are also those which are gaseous only at temperatures above room temperature, that is to say, for example, aromatics such as chlorobenzene, chlorotoluene (o-, m-, p-isomers), dichlorobenzene (o-, m-, p-isomers), toluene, xylene (o-, m-, p-isomers), chloronaphthalene (all isomers) or decahydronaphthalene. In the group of substances which are already gaseous at room temperature, nitrogen is particularly preferred, because this meets the criteria with respect to chemical inertness extremely well and is considerably less expensive than noble gases here. In the group of substances which are gaseous only above room temperature, substances which are also used as a solvent in the process are preferred. Chlorobenzene and dichlorobenzene are particularly preferred. Of all conceivable inert substances, nitrogen is most preferred.

In a particularly preferred embodiment of the present invention, a diluent containing an inert substance which is already gaseous at room temperature, preferably $N_2$, He, Ar, particularly preferably $N_2$, is employed. Apart from the inert substance, the diluent also contains at least oxygen, and in particular in concentrations of between 0.0001% by weight and ≤10.0000% by weight, preferably between 0.0050% by weight and 1.0000% by weight, particularly preferably between 0.0100% by weight and 0.5000% by weight, based on the weight of the diluent. On the basis of the acceptable low purity of the diluent of only ≥90.0000%, preferably ≥99.0000%, particularly preferably ≥99.5000%, less expensive processes can be used for producing the diluent, as a result of which the costs of obtaining the diluent are reduced and the profitability of the process for the preparation of isocyanates is increased. Diluents with a lower purity often also contain, in addition to oxygen, other substances which do not necessarily interfere in the vaporization of the amine. Thus e.g. nitrogen of lower purity may also contain argon, helium and water.

In the process according to the invention, the oxygen content of the diluent to be employed is preferably determined before introduction thereof into the vaporization space. This also includes taking note of analysis certificates from the particular suppliers of the diluents if these are bought in by the isocyanate producer without his own analysis. If oxygen-containing gases, such as nitrogen or argon, preferably nitrogen, are employed as diluents, the oxygen content of the diluent is preferably determined by a gas chromatography online analysis familiar to the person skilled in the art.

If the analysis of the oxygen content of the diluent shows that feeding an originally sought volume flow of this diluent into the vaporization space with a given volume flow of amine would lead to a molar ratio of amine to oxygen of less than 1,000:1, preferably less than 10,000:1. the following possibilities result:

a) Reduction of the volume flow of diluent under the framework condition that in the vaporization space the conditions do not fall below the minimum content of >0.10% by weight of diluent, based on the total weight of amine and diluent. In this embodiment, the molar ratio of amine to oxygen ($O_2$) in step (i) (conversion of the amine into the gas phase) in the vaporization space of ≥1,000:1, preferably in the range between 1,000:1 and 1,000,000:1, particularly preferably between 10,000:1 and 50,000:1 is maintained by reducing the absolute volume flow of the diluent fed to the vaporization space (in this context see also Example 3).

Or:

b) Mixing of the batch of the diluent of too low purity with another, purer batch of the diluent in a ratio such that feeding of the volume flow of diluent originally sought into the vaporization space can be carried out with the mixed batch obtained in this way without falling below the minimum molar ratio of amine to oxygen of 1,000:1. In this embodiment, the diluent employed in step (i) (conversion of the amine into the gas phase) is accordingly a mixture of various batches of the diluent with various oxygen contents. The purer batch of the diluent can be obtained, for example, by recovering and recycling diluent which has already passed through the reaction space, the oxygen it contains having been eliminated by reaction with amine or other substances present in the reaction mixture.

Any desired suitable vaporizers can in principle be employed as vaporizers for the amine vaporization. Tube bundle heat exchangers, plate heat exchangers or falling film vaporizers, optionally with pumped circulation, can preferably be employed. Micro heat exchangers or micro vaporizers as described in WO 2005/016512 A or in DE 10 2005 036870 A1 can also be employed. Preferably, vaporization systems in which a small work content is led with a high circulating output over a falling film vaporizer are employed. Preferably, those vaporization systems in which a continuous discharge of liquid from the vaporizer takes place are furthermore employed.

The conversion according to the invention of amines into the gas phase is primarily of importance for the gas phase phosgenation of amines to give the corresponding isocyanates. The considerations regarding the purity of the diluent can also be applied in principle, however, to other uses of the amine vaporization. In the case of TDA, other uses of the amine vaporization include e.g. vaporization for the purpose of distillation, such as, for example, the separation of ortho- and meta-TDA isomers, or removal of TDA residue by distillation. Other uses of TDA vaporization can also include uses in which TDA is only partially vaporized, e.g. in driving out dissolved gases, such as, for example, ammonia, with an inert gas. Partial vaporization also exists during storage and transportation of TDA in the molten state, where inert gases can be employed for blanketing.

In the process according to the invention, both the vaporization of the amine and a superheating which may be necessary can be carried out in one stage; but they can also each be carried out in several stages. After the first or, where appropriate, single superheater, the vaporous amine stream can be passed through a drop separator. Alternatively, it is also possible for the vaporous amine stream already to be passed through a drop separator after the vaporizer.

The average dwell time from leaving the vaporization space to entry into the reaction space is more than 0.01 second, preferably more than 0.1 second and particularly preferably more than 0.5 second. Preferably, the dwell time to entry into the reaction space is not more than 60 seconds. This dwell time is sufficiently long at the given temperatures in the vaporization to ensure that the oxygen present in the inert diluent fed to the vaporization reacts completely with the amine.

The vaporizers and/or superheaters and the pipelines for generation of the vaporous diamine stream to the gas phase reactor can be produced from any desired metallic material, e.g. steel, high-grade steel, titanium, Hastelloy, Inconel or other metallic alloys.

The reaction of the primary amine with phosgene is carried out in at least one reaction space arranged in a reactor. Reaction space is understood as meaning the space in which the gas phase reaction of primary amine (or intermediate products) with phosgene to give the desired isocyanate takes place. Reactor is understood as meaning the technical device which contains the reaction space. A reactor here can also contain several reaction spaces. Several reactors with in each case one or more reaction spaces can also be connected in series or in parallel.

The process according to the invention can in principle be applied to any reaction space and reactor geometry.

In a further preferred embodiment of the process according to the invention, the reactor has, after the reaction space in which, after mixing of the educts, a conversion of the amine groups into the isocyanate groups of 80.0%, preferably 90.0%, particularly preferably 99.0%, very particularly preferably 99.5% is achieved, a further rotationally symmetric reaction space with a constant and/or widened flowed-through cross-sectional area.

The process according to the invention can in principle be applied to any procedure of gas phase phosgenation. The adiabatic procedure described in EP 1 935 876 A1 is preferred. However, the process described can also be applied to an isothermal procedure.

The dwell time chosen for reaction of the amine groups with the phosgene to give the isocyanate is preferably between 0.050 second and 15 seconds, depending on the nature of the amine employed, the start temperature, where appropriate the adiabatic increase in temperature in the reaction space, the molar ratio of amine employed and phosgene, the nature and amount of the at least one inert substance and the reaction pressure chosen.

In the process according to the invention, it is advantageous to employ phosgene in excess with respect to the amine groups to be reacted. Preferably, a molar ratio of phosgene to amine groups of from 1.1:1 to 20:1, particularly preferably from 1.2:1 to 5:1 is present. The phosgene is heated to temperatures of from 200° C. to 600° C. and optionally fed to the reaction space in a form diluted with an inert gas, such as $N_2$, He, Ar, or with the vapours of an inert solvent, e.g. aromatic hydrocarbons, without or with halogen substitution, such as e.g. chlorobenzene or dichlorobenzene. If a diluent is likewise added to the phosgene, the oxygen content thereof must be kept as low as possible (as a rule lower than the oxygen content of the diluent for the amine), since oxygen in the phosgene can lead to the formation of residues in the reaction space or even to the formation of explosive mixtures after so-called quenching (see below). Preferably, recycled and thus oxygen-free inert substance is therefore employed for dilution of the phosgene.

After the phosgenation reaction has taken place in the reaction space, the gaseous reaction mixture, which preferably comprises at least one isocyanate, phosgene, an inert substance and hydrogen chloride, is preferably freed from the isocyanate formed. This can be carried out, for example, by subjecting the reaction mixture continuously leaving the reaction space to a condensation in an inert solvent, as has already been recommended for other gas phase phosgenations (EP 0 749 958 A1).

Preferably, however, the condensation is carried out by a procedure in which the reaction space employed in the process according to the invention has at least one zone into which one or more suitable streams of liquid ("quench liquids") are sprayed for discontinuation of the reaction of the amines employed and the phosgene to give the corresponding isocyanates. By this means, as described in EP 1 403 248 A1, rapid cooling of the gas mixtures can be carried out without the use of cold surfaces.

In a particularly preferred form of the process according to the invention, the at least one zone (cooling zone) is integrated into a quenching stage, such as has been disclosed e.g. in EP 1 403 248 A1. In a particularly preferred form, several cooling zones are employed. Integration and operation of these at least two cooling zones are preferably effected with a quenching stage. This is disclosed with respect to construction and operation in EP 1 935 875 A1.

Instead of the integrated combination of the at least one cooling zone of a reactor with a quenching stage, such as has been disclosed in EP 1 935 875 A1, the corresponding integrated combination of the cooling zones of several reactors with a quenching stage is likewise possible. However, the integrated combination of a reactor with at least one cooling zone with a quenching stage is preferred.

The solutions or mixtures leaving the condensation or quenching stage are then preferably worked up by distillation and the isocyanate is obtained in the required purity in this way.

The gas mixture leaving the condensation or quenching stage is preferably freed from residual isocyanate in a downstream gas wash with a suitable wash liquid, and is preferably then freed from excess phosgene in a manner known per se. This can be carried out by means of a cold trap, absorption in an inert solvent (e.g. chlorobenzene or dichlorobenzene) or by adsorption and hydrolysis on active charcoal. The hydrogen chloride gas passing through the phosgene recovery stage can be recycled in a manner known per se for recovery of the chlorine required for the phosgene synthesis. The wash liquid obtained after its use for the gas wash can then preferably be at least partially employed as the quench liquid for cooling the gas mixture in the corresponding zone of the reaction space.

If an inert gas and not the vapour of an inert solvent has been employed as a diluent, the inert gas passes through the condensation or quenching stages and the optionally subsequent gas wash and phosgene recovery in gaseous form together with the gaseous hydrogen chloride. The gaseous hydrogen chloride can be separated off e.g. by absorption in water and the inert gas employed in the vaporization can be recovered in this way. In a preferred embodiment of the process according to the invention, this stream of the inert gas—optionally after drying and optionally after destruction of remaining traces of phosgene—is recycled into the vaporization space to facilitate the conversion of the amine into the gas phase. This stream of the inert gas is free from oxygen here, since oxygen originally present has already reacted with the amine before the reactor for the gas phase phosgenation. Any losses of inert gas can be topped up with fresh diluent, which preferably contains the same inert gas, it being possible for the fresh diluent employed for the topping up to have a high oxygen content of up to 10% by weight, since this gas stream is diluted with the oxygen-free recycled gas. In all cases, the content of oxygen in the inert gas employed as the diluent must be such that the molar ratio of amine to oxygen according to the invention of ≥1,000:1, preferably in the range between 1,000:1 and 1,000,000:1, particularly preferably between 10,000:1 and 50,000:1, is maintained. In this embodiment, the diluent employed in step (i) (conversion of the amine into the gas phase) accordingly at least partially contains the inert substance recycled after the reaction to give the isocyanate has taken place in step (ii).

In the process according to the invention, those primary amines which can be converted into the gas phase essentially without decomposition are preferably employed.

Examples of preferred aliphatic or cycloaliphatic amines are 1,4-diaminobutane, 1,6-diaminohexane (HDA), 1,11-diaminoundecane, 1-amino-3,5,5-trimethyl-3-aminomethyl-cyclohexane (IPDA), 4,4'-diaminodicyclohexylmethane or 4,4'-diaminodicyclohexyl-2,2-propane. However, diamines of the abovementioned type with exclusively aliphatically or cyclolaliphatically bonded amino groups are particularly preferred, such as isophoronediamine (IPDA), hexamethylenediamine (HDA) or bis(p-aminocyclohexyl)methane (PACM 20).

Examples of preferred aromatic amines are toluoylenediamine (TDA), in particular 2,4-TDA and 2,6-TDA and mixtures thereof, diaminobenzene, naphthyldiamine (NDA) and 2,2'-, 2,4'- or 4,4'-methylenediphenyldiamine (MDA) or isomer mixtures thereof. Toluylenediamine (TDA), in particular 2,4-TDA and 2,6-TDA and mixtures thereof, is particularly preferred. 2,4-/2,6-TDA isomer mixtures with isomer ratios of 80/20 and 65/35 are very particularly preferred.

EXAMPLES

General Conditions in all the Examples

Dried air and four nitrogen sources of different purity, as diluents, are available:
Example 1: >99.999% purity (<0.0001% by weight of $O_2$)

Example 2: 99.32% purity (0.68% by weight of $O_2$)
Examples 3 and 4: 98.09% purity (1.91% by weight of $O_2$)
Example 5: 92.12% purity (7.88% by weight of $O_2$)
Example 6: dried air (78% by weight of $N_2$, 22% by weight of $O_2$)

Employing these diluents, an m-toluoylenediamine isomer mixture containing 80.3% of 2,4-TDA and 19.7% of 2,6-TDA is to be vaporized. For this, approx. 100 g of the TDA isomer mixture are weighed accurately into a 250 ml round-bottomed flask which is connected to a distillation apparatus which can be operated under reduced pressure and comprises a Reitmeyer attachment, bridge and cooled distillation receiver. A boiling capillary which ends immediately above the level of liquid of the TDA isomer mixture introduced projects into the round-bottomed flask. The diluent is passed into the round-bottomed flask via this boiling capillary at 4 and, respectively, 10 l/h (under 1013 hPa at 20° C.), while the flask is heated by means of a hot air fan. The TDA vapour which forms is fed together the diluent under an absolute pressure of 100 mbar through the Reitmeyer attachment and bridge into the distillation receiver and is condensed and collected there. The distillation is carried out until the TDA initially introduced has vaporized completely. Under the absolute pressure established of 100 mbar, this is the case after a time of from 16 to 17 minutes, and can also be seen by the fact that the internal temperature in the round-bottomed flask exceeds 180° C. The molar amount of oxygen with which the TDA vapour came into contact can be calculated from the duration of the distillation and the known volume stream of the diluent.

If oxidation products of which the boiling point is not substantially higher than that of m-TDA are formed by the contact between TDA vapour and oxygen, these enter into the distillation receiver, where their content can be determined by a residue distillation of the distillate collected.

If oxidation products of which the boiling point is substantially higher than that of m-TDA are formed by the contact between TDA vapour and oxygen, these remain in the round-bottomed flask or in the Reitmeyer attachment and can be back-weighed there.

Example 1

Comparative Example: Oxygen Content of the Diluent<0.0001% by Weight; Molar Ratio of Amine:Oxygen>1,000:1

During distillation of 101.6 g of m-TDA (0.83 mol) for 17 minutes, 10 l/h of nitrogen were added to the TDA vapour as a diluent. In accordance with the prior art for gas phase phosgenation, the nitrogen had an oxygen content of <0.0001% by weight (corresponds to 1 ppm), namely of 0.62 ppm. The amount of oxygen introduced is thus negligibly small, so that the molar ratio of m-TDA to oxygen is considerably greater than 1,000:1.

The amount of residue in the round-bottomed flask was 1,300 mg, the amount of residue in the distillation receiver was 70 mg.

Example 2

According to the Invention: Oxygen Content of the Diluent>0.0001% by Weight; Molar Ratio of Amine:Oxygen>1,000:1

The procedure is just as in Example 1. During distillation of 109.4 g of m-TDA (0.90 mol) for 16.25 minutes, 10 l/h of nitrogen with 0.68% by weight of oxygen were employed. The molar ratio of amine to oxygen is mathematically 1,173:1. The amount of residue in the round-bottomed flask was 1,286 mg, the amount of residue in the distillation receiver was 73 mg. The residue values are practically identical to those in Example 1, and the yield is thus just as good as when pure nitrogen is employed.

Example 3

According to the Invention: Oxygen Content of the Diluent>0.0001% by Weight; Molar Ratio of Amine:Oxygen>1,000:1—Reduction of the Absolute Amount of Diluent The procedure is just as in Example 1. During distillation of 106.2 g of m-TDA (0.87 mol) for 16.25 minutes, only 4 l/h of nitrogen with 1.91% by weight of oxygen were employed. Due to the smaller amount of diluent, the molar ratio of amine to oxygen is still greater than 1,000, namely mathematically 1,010:1. The amount of residue in the round-bottomed flask was 1,296 mg, the amount of residue in the distillation receiver was 72 mg. Both residue values are just as low as when pure oxygen is used in Example 1.

Example 4

Comparative Example: Oxygen Content of the Diluent>0.0001% by Weight; Molar Ratio of Amine:Oxygen<1,000:1

The procedure is just as in Example 3. During distillation of 105.6 g of m-TDA (0.86 mol) for 17 minutes, 10 l/h of nitrogen with 1.91% by weight of oxygen were employed. The molar ratio of amine to oxygen is now mathematically 384:1. The amount of residue in the round-bottomed flask was 1,408 mg, the amount of residue in the distillation receiver was 81 mg. Both residue values are increased significantly compared with Example 1 to 3, which would manifest itself as a loss in yield in a large-scale industrial procedure. The example shows that the change in the molar ratio of m-TDA to oxygen to a value of less than 1,000 has an adverse effect on the yield.

Example 5

Comparative Example: Oxygen Content of the Diluent>0.0001% by Weight; Molar Ratio of Amine:Oxygen<1,000:1

The procedure is just as in Example 1. During distillation of 106.0 g of m-TDA (0.87 mol) for 17 minutes, 10 l/h of nitrogen with 7.88% by weight of oxygen were employed. The molar ratio of amine to oxygen is mathematically 93:1. The amount of residue in the round-bottomed flask was 1,393 mg, the amount of residue in the distillation receiver was 91 mg. Both residue values are increased significantly compared with Example 1 to 3, which would manifest itself as a loss in yield in a large-scale industrial procedure. Compared with Example 1, the residue in the distillation receiver (content of oxidation products, the boiling point of which is not substantially higher than that of m-TDA) is increased by 30%, which in the large-scale industrial procedure of this process can lead to accelerated blocking of the lines carrying TDA vapour, in addition to losses in yield.

Example 6

Comparative Example: Oxygen Content of the Diluent 22% by Weight; Molar Ratio of Amine:Oxygen<1,000:1

During distillation of 112.5 g of m-TDA (0.92 mol) for 17 minutes, 10 l/h of dried air were added to the TDA vapour as a diluent. The molar ratio of amine to oxygen is mathematically 37:1. Oxidation products were formed, the boiling point of which is not substantially higher than that of m-TDA, which was to be observed in a clear discoloration of the m-TDA collected in the distillation receiver. Formation of oxidation products with a substantially higher boiling point, which remain in the round-bottomed flask as the residue, also occurred.

The amount of residue in the round-bottomed flask was 1,477 mg, the amount of residue in the distillation receiver was 113 mg. This means, compared with Example 1, an increase of 13% in the round-bottomed flask (oxidation products with a substantially higher boiling point than m-TDA) and of 61% in the distillation receiver (oxidation products of which the boiling point is not substantially higher than that of m-TDA). The clear increase in oxidation products, the boiling point of which is not substantially higher than that of m-TDA, would, in the large-scale industrial procedure of this process, would lead to accelerated blocking of the lines carrying TDA vapour, in addition to losses in yield.

Table 1 summarizes for Examples 1 to 6 how the formation of oxidation products with a boiling point similar to or substantially higher than m-TDA depends on the ratio of m-TDA to oxygen during the distillation.

TABLE 1

| Example | Molar ratio of m-TDA: oxygen | Amount of diluent [l/h] | Oxygen content of diluent [% by weight] | Residue in distillation bottom product [mg] | Residue in distillate [mg] |
|---|---|---|---|---|---|
| 1 | >>1,000 | 10 | <0.0001 | 1,302 | 70 |
| 2 | 1,173 | 10 | 0.68 | 1,286 | 73 |
| 3 | 1,010 | 4 | 1.91 | 1,296 | 72 |
| 4 | 384 | 10 | 1.91 | 1,408 | 81 |
| 5 | 93 | 10 | 7.8 | 1,393 | 91 |
| 6 | 37 | 10 | 22 | 1,477 | 113 |

The invention claimed is:

1. Process for the preparation of isocyanates by reaction of the corresponding amines with phosgene in the gas phase, wherein
   (i) the amine is converted into the gas phase in a vaporization space in the presence of from >0.10% by weight to 10% by weight of a diluent, based on the total weight of diluent and amine;
   (ii) the gaseous stream obtained from (i) containing amine and diluent is reacted with a gaseous phosgene stream in a reaction space to give the corresponding isocyanate;
characterized in that
   the diluent employed in step (i) contains between 90.0000% by weight and 99.9950% by weight of substances which are inert in the phosgenation process and between 0.68% by weight and 10.0000% by weight of oxygen, in each case based on the weight of the diluent, and
   the molar ratio of amine to oxygen ($O_2$) in step (i) in the vaporization space is in the range between 1,000:1 and 1,000,000:1;
wherein the amine is toluene diamine (TDA).

2. Process according to claim 1, in which in step (i) the amine is converted into the gas phase in the presence of >0.10% by weight to 10% by weight of a diluent which contains between 99.0000% by weight and 99.9950% by weight of substances which are inert in the phosgenation process and between 0.68% by weight and 1.0000% by weight of oxygen, in each case based on the weight of the diluent.

3. Process according to claim 1, in which in step (i) the amine is converted into the gas phase in the presence of >0.20% by weight to 5.0% by weight of a diluent which contains between 99.5000% by weight and 99.9900% by weight of substances which are inert in the phosgenation process and between 0.68% by weight and 0.5000% by weight of oxygen, in each case based on the weight of the diluent, and wherein the molar ratio of amine to oxygen in the vaporization space is in the range between 10,000:1 and 50,000:1.

4. Process according to claim 1, in which the molar ratio of amine to oxygen ($O_2$) in step (i) in the vaporization space of ≥1,000:1 is maintained by reducing the absolute volume flow of the diluent fed to the vaporization space.

5. Process according to claim 1, in which the diluent employed in step (i) at least partially contains the inert substance recycled after the reaction to give the isocyanate has taken place in step (ii).

6. Process according to claim 1, in which the substance which is inert in the phosgenation process is nitrogen.

7. Process according to claim 1, in which the diluent contains between 0.68% by weight and 1.91% by weight of oxygen.

8. Process according to claim 1, wherein the dwell time for reaction of the amine with the phosgene is from 0.050 seconds and 15 seconds.

9. Process for the preparation of isocyanates by reaction of the corresponding amines with phosgene in the gas phase, wherein
   (i) the amine is converted into the gas phase in a vaporization space in the presence of from >0.10% by weight to 10% by weight of a diluent, based on the total weight of diluent and amine;
   (ii) the gaseous stream obtained from (i) containing amine and diluent is reacted with a gaseous phosgene stream in a reaction space to give the corresponding isocyanate;
characterized in that
   the diluent employed in step (i) contains between 90.0000% by weight and 99.9950% by weight of substances which are inert in the phosgenation process and between 0.68% by weight and 1.91% by weight of oxygen, in each case based on the weight of the diluent, and
   the molar ratio of amine to oxygen ($O_2$) in step (i) in the vaporization space is in the range between 1,000:1 and 1,000,000:1;
wherein the amine is toluene diamine (TDA).

10. The process according to claim 1, wherein the substance which is inert in the phosgenation process is selected from the group consisting of noble gases, carbon dioxide, aromatics, nitrogen and combinations thereof.

11. The process according to claim 9, wherein the substance which is inert in the phosgenation process is selected from the group consisting of noble gases, carbon dioxide, aromatics, nitrogen and combinations thereof.

* * * * *